United States Patent [19]

Lai

[11] 4,240,961
[45] Dec. 23, 1980

[54] SYNTHESIS OF 2-PIPERAZINONES AND 1,4-DIAZA-2-KETO-CYCLOHEPTANES

[75] Inventor: John T. Lai, Broadview Hgts., Ohio

[73] Assignee: The B. F. Goodrich Company, Akron, Ohio

[21] Appl. No.: 43,294

[22] Filed: May 29, 1979

[51] Int. Cl.$^3$ .................. C07D 243/08; C07D 241/18
[52] U.S. Cl. .............................. 260/239.3 R; 544/384
[58] Field of Search .................. 260/239.3 R; 544/384

[56] References Cited

U.S. PATENT DOCUMENTS

| | | | |
|---|---|---|---|
| 2,649,450 | 8/1953 | Strong et al. | 544/384 |
| 2,700,668 | 1/1955 | Strong et al. | 544/384 |
| 4,167,512 | 9/1979 | Lai | 260/239.3 R |

Primary Examiner—Henry R. Jiles
Assistant Examiner—Robert T. Bond
Attorney, Agent, or Firm—Alfred D. Lobo; J. Hughes Powell, Jr.

[57] ABSTRACT

Substituted 2-piperazinones are prepared by reacting a substituted 1,2-diamine with (a) an acyclic or cyclic cyanohydrin acetate, (b) a haloform, and (c) alkali metal hydroxide, in the presence of a suitable organic solvent, at ambient pressure and temperature preferably lower than about 20° C. In an analogous manner, substituted 1,4-diaza-2-keto-cycloheptanes are prepared by reacting substituted 1,3-propane-diamines. In this synthesis, referred to as "the cyanohydrin acetate synthesis," the reaction is accelerated with a phase transfer catalyst selected from the group consisting of a polyether, an onium salt, and a tertiary amine. This synthesis yields predominantly a 2-keto-diazacycloalkane with substituents desirably substituted on carbon atoms on either side of the $N^4$ atom of the diaza ring.

9 Claims, No Drawings ical weight, and subject to degradation by UV light. These may be natural or synthetic organic materials.

SYNTHESIS OF 2-PIPERAZINONES AND 1,4-DIAZA-2-KETO-CYCLOHEPTANES

BACKGROUND OF THE INVENTION

Organic materials, whether natural or synthetic, are conventionally protected against degradation by ultraviolet (UV) light by incorporating a UV light stabilizer in the material. Many classes of compounds are known to be useful UV light stabilizers, some being more effective than others. Particularly effective compounds which provide compositions resistant to degradation by UV light, include the decahydroquinolines disclosed in U.S. Pat. Nos. 3,919,234; 3,920,659; 3,928,330; 4,069,195; and, 4,073,770; 1,5-diazacycloalkanes and 2-keto-1,5-diazacycloalkanes disclosed in copending U.S. Pat. application Ser. No. 835,069; and, the 2-keto-1,4-diazacycloalkanes disclosed in copending U.S. Pat. application Ser. No. 835,065. Other cycloalkanes useful as UV light stabilizers are disclosed in German Offen. No. 2,315,042; and, Japanese Pat. Nos. 7,453,571 and 7,453,572.

The foregoing compounds appear to derive their effectiveness as UV stabilizers from their mono-keto structure, that is a 2-keto-1,4-diazacycloalkane structure, in which a total of two or more (hence "polysubstituted") substituents are provided on the carbon atoms on either side of, and immediately adjacent the $N^4$ atom of the diaza ring (hereafter referred to as "the $N^4$-adjacent C atoms"). Even on a laboratory scale, polysubstituted 2-piperazinones with substituents on the $N^4$-adjacent C atoms are difficult to prepare, particularly if they are to be formed to the substantial exclusion of compounds which do not contain substituents on the $N^4$-adjacent C atoms. For example, the polysubstituted 1,4-diaza-2-keto-cycloalkanes disclosed in the aforementioned references, and also the dispiro substituted diazacyclohexanes arduously synthesized in U.S. Pat. No. 4,097,452 to Mayer et al., can be conveniently and economically prepared, with the ratio of substituted compounds having substituents on the $N^4$-adjacent C atoms to those without substituents on these C atoms, being in excess of 20:1 by weight. In copending U.S. Pat. application Ser. No. 916,640 now issued as U.S. Pat. No. 4,167,512 several methods are disclosed for preparing various substituted piperazin-2-ones and 1,4-diaza-2-keto-cycloheptanes, all of which methods are incorporated by reference thereto as if fully set forth herein.

The effectiveness of the instant reaction, referred to as "the cyanohydrin acetate synthesis," is particularly noteworthy because it is known that a hydroxyl group will react with dichlorocarbene, but it is quite unexpected that an acetate group would react in the same way. Hydroxyl and acetate groups are known not to behave similarly in most reactions. Further, because of the presence of alkali metal hydroxide, acetone cyanohydrin forms an anion which appears to be essential for the completion of the cyclization of the diaza ring. However, acetone cyanohydrin acetate does not form such an anion, whether in the presence of alkali or not, so that the cyanohydrin acetate would not be expected to react in a manner analogous with cyanohydrin.

Particular reference is made to a known synthesis referred to as "the cyanohydrin synthesis," wherein a substituted 1,2-diamine is reacted in an organic solvent medium with cyclic or acyclic cyanohydrins in the presence of an "onium salt" (defined hereinafter) catalyst, to yield a polysubstituted 2-keto-1,4-diazacycloalkane. The cyanohydrin acetate synthesis of this invention is an improvement of the aforementioned cyanohydrin synthesis.

SUMMARY OF THE INVENTION

It has been discovered that polysubstituted 2-keto-1,4-diazacycloalkanes may be prepared under substantially ambient conditions, from substituted diamines and cyanohydrin acetates in the presence of alkali, all of which starting materials are readily available, in conventional apparatus, with excellent yields of desirable, highly effective stabilizer compounds.

More specifically, it has been discovered that polysubstituted 2-keto-1,4-diazacyclohexanes and 2-keto-1,4-diazacycloheptanes wih substituents on the $N^4$-adjacent C atoms are obtained in excellent yield, with very little formation of undesirable polysubstituted compounds, when a substituted 1,2-diamine or substituted 1,3-propane-diamine is reacted with a cyclic or acyclic cyanohydrin acetate, chloroform or bromoform, and either solid alkali or aqueous alkali, in the presence of an organic solvent medium for the reactants. The reaction is accelerated by certain known phase transfer catalysts; among these are polyethers, onium salts and tertiary amines.

The novel synthesis of this invention referred to as "the cyanohydrin acetate synthesis," utilizes a reaction which involves the acetate group in much the same way as the aforementioned known cyanohydrin synthesis utilizes a reaction which involves the hydroxyl group. The discovery of analogous reactions of the hydroxyl and acetate group is quite surprising since it is well-known that these groups have separate and distinct reactive characteristics.

DETAILED DESCRIPTION OF PREFERRED EMBODIMENTS

The basic structure of the compounds prepared by the synthesis described herein, is a polysubstituted 1,4-diaza-2-keto-cycloalkane having (a) a fixed two-carbon bridge between the two N atoms (the $N^1$ and $N^4$ atoms) of the diaza ring, the remaining portion of the ring having a variable length bridge of two or three carbon atoms, (b) an $N^1$-adjacent carbonyl in the fixed two-carbon bridge, and (c) each of the $N^4$-adjacent C atoms has two substituents (hence "polysubstituted"), which may be cyclizable, that is, form a cyclic substituent. These polysubstituted compounds may be (i) monocyclic with at least four acyclic substituents on the diaza ring, two of which are on each $N^4$-adjacent C atom; or (ii) with cyclizable substituents, the compounds may include one, two or more spiro substituents, thus presenting a structure with two, or three, or more unfused rings; and, (iii) the compounds may form dimers and bis-compounds. The diaza ring of the basic structure has either 6 or 7 ring members, that is, they are either substituted piperazin-2-ones, or, 1,4-diaza-2-keto-cycloheptanes (also termed "2-keto-diazepines"), or, dimers or bis-compounds thereof. These substituted 1,4-diaza-2-keto-cycloalkanes are especially effective UV stabilizers in substantially colorless organic materials.

As stabilizers the aforementioned 2-keto compounds are used in the range from about 0.01 to about 5 parts by weight, and preferably from about 0.1 to about 1.0 part per one hundred parts (phr) of organic material subject to UV light. These materials may be low or high molecular weight materials, and particularly include homopolymers, copolymers and mixtures thereof. Examples of materials that can be stabilized against degradation due to UV light are oils; monomers, particularly $\alpha\beta$-olefinically unsaturated monomers such as acrylates, dienes, vinyl nitriles, and the like; and other relatively lower molecular weight materials than synthetic resinous polymers, such as alcohols, aldehydes, and the like. Examples of known materials which can be stabilized with polysubstituted 2-keto-1,4-diazacycloalkanes are natural rubber, synthetic rubbers such as cis-polyisoprene, styrene-butadiene rubber, diene-nitrile rubbers, polyepihalohydrin polymers, polyurethanes, PVC resins, ABS resins, polystyrene, polyacrylonitrile, polymethacrylates, polycarbonates, varnish, phenol-formaldehyde resins, polyepoxides, polyesters, and polyolefin homo and copolymers such as polyethylene, polypropylene, ethylene-propylene polymers, ethylene-propylenediene polymers, ethyl-vinyl acetate polymers, and the like. The substituted 2-keto-1,4-diazacycloalkanes can also be used to stabilize mixtures and blends of polymeric materials such as ABS resin blends, PVC and polymethacrylate blends, and blends of polyolefin homopolymers and copolymers such as blends of polypropylene in epdm polymers.

The 2-keto-1,4-diazacycloalkanes prepared by the synthesis of this invention have the structural formula:

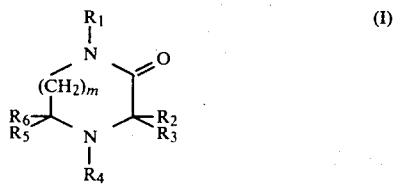

(I)

wherein, m represents an integer which is 1 or 2, being the number of methylene groups forming a bridge of variable length in the diaza ring, so that, when m is 1 then (I) represents a polysubstituted piperazin-2-one, and when m is 2, then (I) represents a polysubstituted 2-keto-1,4-diazepin;

$R_1$ and $R_4$ independently represent hydrogen, alkyl having from 1 to about 24 carbon atoms, hydroxyalkyl having from 1 to about 12 carbon atoms, haloalkyl having from 1 to about 12 carbon atoms, cyanoalkyl having from 2 to about 12 carbon atoms, aminoalkyl having from 1 to about 12 carbon atoms, ether groups having from 3 to about 18 carbon atoms, hydroxyalkyl ether or cyanoalkyl ether groups having from 4 to about 18 carbon atoms, alkenyl or aralkyl having from 7 to about 14 carbon atoms, alkylene having from 2 to about 7 carbon atoms and optionally containing a phosphite, ester or hindered phenol group; and, $R_2$ and $R_3$ on the $N^4$-adjacent carbon of the fixed two-carbon bridge, and, $R_5$ and $R_6$ on the $N^4$-adjacent carbon atom of the variable length bridge, independently each represent alkyl having from 1 to about 12 carbon atoms, haloalkyl having from 1 to about 12 carbon atoms, cyanoalkyl having from 2 to about 12 carbon atoms, aminoalkyl having from 2 to about 12 carbon atoms, cycloalkyl having from 5 to about 8 carbon atoms, hydroxy-cycloalkyl having from 5 to about 8 carbon atoms, alkenyl and aralkyl having from 7 to about 14 carbon atoms.

It will presently be evident that many of the substituents identified hereinafter may not be made directly by the synthesis of this invention, but by additional steps after having formed the substituted 1,4-diaza-2-keto-cycloalkane. These additional steps are well known to those skilled in the art, and do not require detailed description herein. In particular, dimers and bis compounds of substituted 1,4-diaza-2-keto-cycloalkanes can be prepared by known methods, once the desired 1,4-diaza-2-keto-cycloalkane is obtained by the cyanohydrin acetate synthesis.

Illustrative of the type of substituents that provide effective stabilization in the above-identified 1,4-diaza-2-keto-cycloalkanes are:

where $R_1$ and/or $R_4$ is alkyl, examples are methyl, ethyl, n-propyl, n-butyl, t-butyl, n-hexyl, n-octyl, 2-ethylhexyl, n-decyl, n-tetradecyl, n-octyldecyl, and the like;

where $R_1$ and/or $R_4$ is hydroxyalkyl, examples are 2-hydroxyethyl, 2-hydroxypropyl, 3-hydroxypropyl, 2-hydroxybutyl, 6-hydroxyhexyl, 8-hydroxyoctyl, and the like;

where $R_1$ and/or $R_4$ is haloalkyl, examples are 2-chloroethyl, 2-bromoethyl, 2-fluoroethyl, 2-chlorobutyl, 4-chlorobutyl, 2-chloroethylhexyl, and the like;

where $R_1$ and/or $R_4$ is cyanoalkyl, examples are 2-cyanoethyl, 3-cyanopropyl, 4-cyanobutyl, 8-cyanooctyl, and the like;

where $R_1$ and $R_4$ is aminoalkyl, examples are 2-aminoethyl, 3-aminopropyl, 4-aminobutyl, 6-aminohexyl, 2-methyl-2-aminoethyl, and the like;

where $R_1$ and $R_4$ is ether, examples are methoxyethyl, ethoxyethyl, ethoxypropyl, octyloxyethyl, phenoxyethyl, p-methylphenoxypropyl, and the like;

where $R_1$ and $R_4$ is hydroxyalkylether or cyanoalkyl ether, examples are 2-hydroxyethyloxaethyl, p-(2-hydroxypropyl)-phenyloxapropyl, 4-hydroxybutyloxahexyl, 2-cyanoethyloxaethyl, 2-hydroxyethyl-di(oxaethyl), and the like;

for $R_2$, $R_3$, $R_5$, and $R_6$, examples are methyl, ethyl, propyl, n-butyl, isobutyl, n-hexyl, 2-ethylheptyl, n-decyl, and where the substituents are cyclizable, cyclopentyl, methylcyclopentyl, cyclohexyl, methylcyclohexyl, dimethyl cycloheptyl, piperidyl, 2-2',6-6'-tetramethyl piperidyl, and the like.

Examples of specific substituted mono-keto-diazacycloalkan-2-ones derived from compounds prepared by the synthesis of this invention, wherein the $N^4$-adjacent C atom of the fixed two carbon bridge has two substituents which may be cyclizable, are:

(a) diazamonocycloalkan-2-ones having substituents on either N atom, and, four substituents on the diaza ring, for example, $N^1$-isopropyl-3,3,5,5-tetramethyl-2-piperazinone, and, (b) diazamonocycloalkan-2-ones having at least one spiro substituent on either $N^4$-adjacent carbon atom, for example, $N^1$-tert-octyl-5,5-dimethyl-3,3-pentamethylene-2-piperazineone, and, $N^1$-tert-octyl-3,3,5,5-dispiropentamethylene-1,4-diazacyclohexane.

The more preferred substituted 1,4-diaza-2-keto-cycloalkane compounds are those wherein: $R_1$ and/or $R_4$ is selected from the group consisting of alkyl having from 4 to 18 carbon atoms, benzyl, cyclohexylmethyl, hydroxyalkyl having from 1 to about 6 carbon atoms, hydroxyalkyl ether having from 4 to about 12 carbon atoms, cyanoalkyl having from 2 to about 6 carbon atoms, and aminoalkyl having from 1 to about 6 carbon atoms, $R_2$, $R_3$, $R_5$ and $R_6$ are selected from the group consisting of alkyl having from 1 to about 12 carbon atoms, and polymethylene having from 5 to 6 carbon atoms which are cyclizable; only $R_2$, $R_3$ may be cyclized, or $R_2$, $R_3$ and $R_5$, $R_6$ may be cyclized; and if $R_2$, $R_3$, and $R_5$, $R_6$ are each cyclized, the cyclic substituents may be the same or different; and when the groups adjacent the $N^4$ atom are cyclized, the methylene groups thereof range in number from 4 to about 6.

Examples of the aforespecified more preferred substituted 1,4-diaza-2-keto-cycloalkanes are:

$N^1$-($\beta$-hydroxyethyl)3,3-pentamethylene-5,5-dimethylpiperazin-2-one;

$N^1$-tert-octyl-3,3,5,5-tetramethyl-diazepin-2-one;

$N^1$-tert-octyl-3,3-pentamethylene-5,5-hexamethylene-diazepin-2-one; and, $N^1$-tert-octyl-3,3-pentamethylene-5,5-dimethylpiperazin-2-one.

Examples of the aforespecified more preferred bis compounds of substituted 1,4-diaza-2-keto-cycloalkanes are:

trans-1,2-cyclohexane-bis-($N^1$-5,5-dimethyl-3,3-pentamethylene-2-piperazinone;

and, trans-1,2-cyclohexane-bis-($N^1$-3,3,5,5-dispiropentamethylene-2-piperazinone).

In the synthesis of this invention, substituted 1,2-diamines and 1,3-propane-diamines may be reacted with a cyanohydrin acetate in an organic solvent for the reactants, in the presence of either solid alkali or aqueous alkali, provided there is also present a haloform. By the term "haloform" I refer to chloroform or bromoform particularly, though some reactions will proceed with liquid iodoform. Reaction is accelerated by the presence of a phase transfer catalyst. By the term "phase transfer catalyst" I refer to onium salts, tertiary amines, and polyethers such as are well known to be effective in phase transfer catalyzed reactions, though in such reactions, generally, a catalyst of one type, say an onium salt, may be effective, while a catalyst of either of the other types, or both, may not be effective.

By onium salts, I particularly refer to quaternary amines such as are generally used in the phase transfer catalysis of heterogeneous reactions in immiscible liquids, or between solid and liquid reactants. The necessary requirement for the onium salt chosen is that it be soluble in both liquid phases, where both organic and liquid phases are present, and usually a little more soluble in the organic phase than the aqueous phase. A wide variety of onium salts is effective in this cyanohydrin acetate synthesis. These onium salts include the well-known salts of Group VA of the Periodic Table, and some Group VIA elements such as are disclosed in a review in Angewandte Chemie, International Edition in English, 16 493–558 (August 1977), which review is incorporated herein by reference. Discussed therein are various anion transfer reactions where the onium salt exchanges its original ion for other ions in the aqueous phase, making it possible to carry out chemistry there with the transported anion, including $OH^-$ ions.

The onium salts used in this synthesis include one or more groups having the formula $(R_nY)^+X^-$, wherein Y is either a pentavalent ion derived from an element of Group VA, or a tetravalent ion derived from an element of Group VIA; R is an organic moiety of the salt molecule bonded to Y by four covalent linkages when Y is pentavalent, and three covalent linkages when Y is tetravalent; $X^-$ is an anion which will dissociate from the cation $(R_nY)^+$ in an aqueous environment. The group $(R_nY)^+X^-$ may be repeated as in the case of dibasic quaternary salts having two pentavalent Group VA ions substituted in the manner described.

The preferred onium salts for use in the invention have the formula $(R^1R^2R^3R^4Y^+)X^-$ wherein Y is N or P, and $R^1$–$R^4$ are monovalent hydrocarbon radicals preferably selected from the group consisting of alkyl, alkenyl, aryl, alkaryl, aralkyl, and cycloalkyl moieties or radicals, optionally substituted with suitable heteroatom-containing functional groups. The onium salts are generally selected to be less preferentially less soluble in the less polar of the two distinct liquid phases. Any of the salts disclosed in U.S. Pat. No. 3,992,432 will be found effective, but most preferred are those in which the total number of carbon atoms in $R^1$, $R^2$, $R^3$, and $R^4$ cumulatively range from about 13 to about 57, and preferably range from about 16 to about 30. Most preferred onium salts have Y=N, and hydrocarbon radicals where $R^1$ is $CH_3$, and $R^2$, $R^3$, and $R^4$ are each selected from the group consisting of n-$C_4H_5$; n-$C_5H_{11}$; mixed $C_5H_{11}$; n-$C_6H_{13}$; mixed $C_6H_{13}$; $C_6H_5$; $C_6H_5CH_2$; n-$C_8H_{17}$; n-$C_{12}H_{25}$; n-$C_{18}H_{37}$; mixed $C_8$-$C_{10}$ alkyl; and the like. However, $R^1$ may also be selected from $C_2H_5$, n-$C_3H_7$ and n-$C_4H_9$.

Various counterions may be used, including $Cl^-$, $Br^-$, $I^-$, $NO_3^-$, $SO_4^=$, $HSO_4^-$ and $CH_2CO_2^-$. Most preferred is $Cl^-$.

The polyethers useful as catalysts in this synthesis include cyclic polyethers such as the crown ethers, disclosed in *Agenwandte Chemie*, supra, and acyclic polyethers having the formula

R—O—R′ wherein R and R′ are independently alkyl having from 1 to about 16 carbon atoms, or alkyl containing substituted functional groups such as hydroxy, sulfur, amine, ether, etc. Most preferred polyethers have the formula R—($OCH_2CH_2$)$_r$OR′ wherein R is alkyl having from 1 to about 16 carbon atoms R′ is alkyl having from 1 to about 16 carbon atoms, or H, and r is an integer in the range from 0 to about 300. Most preferred are commonly available polyethers such as: tetraethylene glycol dimethyl ether; polyethylene oxide (mol wt about 5000); poly(ethylene glycol methyl ether); 1,2-dimethoxyethane; diethyl ether; and the like.

Polyether catalysts are especially desirable in this cyanohydrin acetate synthesis because they produce a preponderance of the desired symmetrically substituted isomer, in a reaction which is remarkably free of undesirable byproducts, which reaction proceeds with a relatively mild exotherm so that the reaction is controllable.

The triamines useful as phase transfer catalysts in this synthesis include the alkyl amines and the aryldialkylamines, exemplified by tributylamine and phenyldibutylamine respectively, which are commonly available, wherein each alkyl may have from 1 to about 16 carbon atoms.

The cyanohydrin acetate synthesis may be carried out at any temperature within a wide range from about the freezing point of the reaction mass to about the reflux temperature of the solvent, provided the reaction temperature is below that deleterious to the 1,4-diaza-2-keto-cycloalkane formed. The reaction is of particular interest because it generally proceeds at room temperature, and preferably below about 20° C., at satisfactory speed, and preferentially yields compounds polysubstituted on the $N^4$-adjacent C atoms, rather than compounds which are not so substituted. Typically, compounds substituted on the $N^4$-adjacent C atoms are produced in an amount from about 10 to about 100 times greater, by weight, than compounds not so substituted. The reaction may also be carried out over a wide range of pressure from subatmospheric to superatmospheric, but atomspheric pressure is preferably employed for convenience, and because there appears to be no substantial advantage to be gained from operating at higher pressures.

The substituted 1,2-diamines and substituted 1,3-butane-diamines may have substituents selected from aryl, cycloalkyl having from 4 to about 7 ring members, and alkyl having from 1 to about 30 carbon atoms, and the diamines may include two primary amine moieties, one primary amine moiety and one secondary amine moiety, or two secondary amine moieties. The amine is chosen to provide, upon cyclization of the diaza ring, the desired number of C atoms in the variable length bridge, and also to provide the desired substituents on preselected C atoms of this bridge. It will thus be evident that an appropriately substituted acyclic diamine will be chosen where a monocyclo-1,4-diaza-2-keto-cycloalkane is to be synthesized; and, that a diamine with a cyclic substituent will yield a spiro substituent in the variable length bridge of the diaza ring.

The cyanohydrin acetate chosen may be a cycloalkanone cyanohydrin acetate, dialkyl ketone cyanohydrin acetate, aralkyl ketone cyanohydrin acetate or aldehyde cyanohydrin acetate. Where the cyanohydrin acetate is an alkyl cyanohydrin acetate, optionally with one or more cyclic substituents, it is necessary that the alkyl cyanohydrin acetate have a carbonyl moiety. The substituents on the cyanohydrin acetate chosen will determine the substituents on the $N^4$-adjacent C atom of the fixed two-carbon bridge.

The organic solvent may be any solvent in which the reactants are soluble and include hydrohalomethylenes, particularly hydrochloromethylenes, sulfolane, dibutyl ether, dimethyl sulfone, diisopropyl ether, di-n-propyl ether, 1,4-dioxane, tetrahydrofuran, benzene, toluene, hexane, carbon tetrachloride and the like. Most preferred solvents are hydrochloromethylenes.

The preferred alkali is an aqueous alkali metal hydroxide solution such as concentrated aqueous sodium hydroxide, or potassium hydroxide, preferably in the range from about 20 percent to about 70 percent. The alkali metal hydroxide may be used in solid form, and when so used, is preferably finely divided. The amount used is not critical but it is preferred to use at least one equivalent of alkali per mol of diamine, and generally, more than three equivalents are used. There is no advantage to using aqueous alkali in an amount more than about 75 percent by weight of the reaction mass. In general, a solid reaction product is recovered from the reaction mass.

The presence of a haloform, such as chloroform, iodoform or bromoform appears to take part in the reaction as a reagent, though the precise mechanism or the manner in which the haloform affects the reaction, is not understood. This hypothesis that a haloform is essential is based upon the fact that, when another solvent is substituted for the haloform, the reaction does not proceed without at least a trace of the haloform. The amount of haloform used does not appear to be critical, and only a minor amount by volume, as compared with the volume of organic solvent used, suffices. A preferred amount of haloform is in excess of 20 percent by weight of the reaction mass, and chloroform is most preferred. In many reactions, a large excess of haloform, in the range from about 2 mols to about 20 mols per mol of diamine, will permit this cyanohydrin acetate synthesis to proceed with no phase transfer catalyst, except that the reaction proceeds relatively more slowly than with the phase transfer catalyst present.

It will be evident that the amount of phase transfer catalyst used is not critical, and that its catalytic function appears to be analogous to that in the aforementioned cyanohydrin synthesis. In general, it is sufficient to use no more phase transfer catalyst than about 2 percent by weight of the reaction mass, and it is preferred to use in the range from about 0.1 to about 1 percent by weight.

The following examples serve to illustrate the invention. Where not otherwise stated, parts are given as parts by weight and the temperatures in degrees centigrade.

EXAMPLE 1

A. Preparation of $N^1$-tert-octyl-3,3,5,5-tetramethyl-2-piperazinone

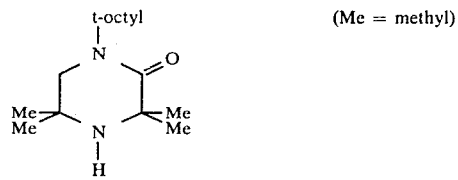

(Me = methyl)

About 2 mols of chloroform are used to dissolve each mol of $N^1$-tert-octyl-2-methyl-1,2-propanediamine in a large flask cooled in an ice-bath. About 1.2mols acetone cyanohydrin acetate, dissolved in dichloromethane, is slowly added to the flask with stirring, and then about 3 mols of conc NaOH(50% by weight) is slowly dripped into the flask, keeping the temperature below about 10° C., followed by the slow addition of a sufficient amount of phase transfer catalyst to produce a controllable reaction. For example, about 0.05 mol benzyltriethylammonium chloride (hereafter "BTAC"), will suffice. The ice is allowed to melt, and the reaction mixture warmed slowly to room temperature. The reaction is complete after several hours, and is then diluted with water to dissolve sodium chloride formed during the reaction. Sufficient water is added to form two distinct phases, one aqueous, and the other organic. The aqueous phase is extracted with dichloromethane, and the extract combined with the organic phase. Further extraction with dichloromethane extracts the substituted 2-piperazinones which are then recovered by concentration and crystallization. The crystals may be dissolved in pentane and recrystallized to yield pure crystals of $N^1$-tert-octyl-3,3,5,5-tetramethyl-2-piperazinone. Essentially no $N^1$-tert-octyl-3,3,6,6-tetramethyl-2-piperazinone is formed. The foregoing structure of the compound is supported by gas chromatograph (GC), infrared (IR), nuclear magnetic resonance (NMR), and mass spectrometer data.

B. In an analogous manner, preselected substituted acyclic alkyl 1,2-diamines may be used to provide the desired substituents on carbon atoms of the variable length bridge. Acyclic substituted alkyl 1,3-propanediamines produce substituents on the $N^4$-symmetrical C atoms of a 2-keto-1,4-diazepine which includes three carbon atoms in the variable length bridge. Similarly, aryl-substituted-1,2-diamines and cycloalkyl-substituted-1,2-diamines may be used to prepare 1,4-diazacycloalkanes with spiro substituents in the variable length bridge.

C. In a manner analogous to that described in Example 1A hereinabove, about 3 mols of solid powdered NaOH are substituted for the aqueous conc NaOH previously used. The reaction proceeds smoothly, though more slowly, with good yield of the desired tetra-substituted compound.

D. The procedure for the synthesis described in Example 1A hereinabove is repeated except that a polyether phase transfer catalyst, poly(ethylene glycol methyl ether), is used instead of the onium salt. The synthesis proceeds with a milder exotherm than when the onium salt catalyst was used, with very little undesired byproducts, and the tetra-substituted compound is formed in excellent yield.

E. The procedure described in Example 1A hereinabove is repeated, except that no phase transfer catalyst is used, and 4 mols more of chloroform are added to the reaction mass in addition to the 2 mols of chloroform previously used. The reaction proceeds slowly but the desired tetra-substituted compound is still formed in good yield.

F. Preparation of $N^1$-tert-octyl-5,5-dimethyl-3,3-pentamethylene-2-piperazinone: In a manner analogous to that described in Example 1A hereinabove, starting with 1 mol of $N^1$-tert-octyl-2-methyl-1,2-propanediamine, about 1.25 mols of cyclohexanone cyanohydrin acetate and 2 mols of $CHCl_3$, and adding conc aqueous NaOH and BTAC, a product is obtained which has a m. pt. of 83°-6° C. Upon analysis, the product is found to be $N^1$-tert-octyl-5,5-dimethyl-3,3-pentamethylene-2-piperazinone.

EXAMPLE 2

A. Preparation of $N^1$-isopropyl-1,4-diazadispiro-(3,3,5,5)pentamethylene-2-piperazinone with an onium salt:

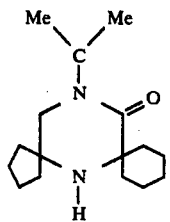

In a manner analogous to that described in Example 1A hereinabove, about 2 mols of $CHCl_3$ are used to dissolve one mol of $N^1$-isopropyl-2,2-pentamethylene-1,2-ethanediamine in a large flask cooled in an ice-bath. About 1.2 mols cyclohexanone cyanohydrin acetate are dissolved in dichloromethane and slowly added to the flask. Then about 3 mols conc aqueous NaOH(50% wt) is slowly dripped into the flask, keeping the contents below about 10° C., followed by the slow addition of about 0.05 mol BTAC phase transfer catalyst. After the reaction is complete the reaction mass is worked up in a manner analogous to that described hereinabove in Example 1A, and the product recovered. The foregoing structure of the compound is supported by the analyses referred to hereinabove in Example 1A.

B. Preparation of $N^1$-isopropyl-1,4-diazadispiro-3,3-pentamethylene-5,5-tetramethylene-2-piperazinone catalyzed with an onium salt:

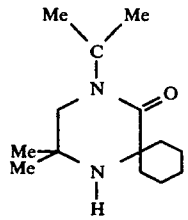

In a manner analogous to that described in Example 2A hereinabove, $N^1$-isopropyl-2,2-tetramethylene-1,2-ethanediamine is substituted for the diamine used in Example 2A. The product obtained is found to have the structural formula illustrated immediately hereinabove. In an analogous manner, other spiro substituents having either the same or different ring members, may be introduced in the 3- and 5-positions of the 1,4-diazacycloalkane synthesized.

C. Preparation of $N^1$-isopropyl-5,5-dimethyl-3,3-pentamethylene-2-piperazinone with a polyether:

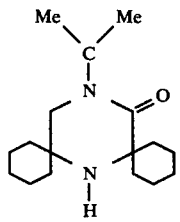

In a manner analogous to that described in Example 2A hereinabove, $N^1$-isopropyl-2-methyl-1,2-propanediamine is substituted for the diamine used in Example 2A, and 1,2-dimethoxy ethane for the onium salt. The product obtained is found to have the structural formula illustrated immediately hereinabove, and has a m. pt. of 102°-4° C.

D. Preparation of trans-1,2-cyclohexane-bis-$N^1$-(dimethyl-3,3-pentamethylene-2-piperazinone) with a trialkylamine

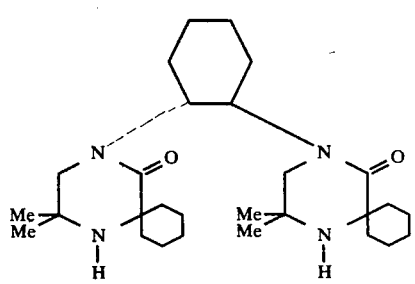

In a manner analogous to that described in Example 2A hereinabove, trans-1,2-cyclohexane-bis-$N^1$-(2-methyl-1,2-propanediamine) is substituted for the diamine used in Example 2A, and 0.05 mol of tributylamine is substituted for the onium salt. The product obtained is found to have the structural formula illustrated immediately hereinabove, and a m. pt. of 270°-2° C.

EXAMPLE 3

A. Preparation of N[1]-octyl-5,5-dimethyl-3,3-pentamethylene-1,4-diazepin-2-one

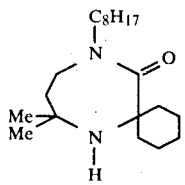

In a manner analogous to that described in Example 1A hereinabove, 1 mol of N[1]-octyl-3-methyl-1,3-butanediamine dissolved in about 2 mols chloroform, and, about 1.2 mols cyclohexanone cyanohydrin acetate dissolved in dichloromethane, are added to a large flask cooled in an ice-bath. Then about 3 mols conc aqueous NaOH are added slowly, along with about 0.05 mol of BTAC. After the reaction is complete a product is recovered which has the structural formula illustrated immediately hereinabove.

B. Preparation of N[1]-octyl-1,4-diazadispiro-(3,3,5,5)pentamethylene-1,5-diazepin-2-one

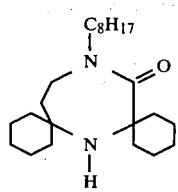

In a manner analogous to that described in Example 2A hereinabove, about 2 mols of chloroform are used to dissolve 1 mol of N[1]-octyl-3,3-pentamethylene-1,3-butanediamine in a large flask cooled in an ice-bath, and, about 1.2 mols of cyclohexanone cyanohydrin acetate dissolved in dichloromethane are added to the flask. Then about 3 mols of conc aqueous NaOH are dripped in followed by about 0.05 mol of BTAC. The reaction is carried out at about ice-bath temperature and the product recovered is found to have the structure illustrated immediately hereinabove.

C. In a manner analogous to that described in Examples 3A and 3B hereinabove, other substituted 1-3-propanediamines with aryl, or cycloalkyl substituents having 4 ring members or as many as 7 ring members, may be used as starting materials to provide aryl and desired cycloalkyl substituents on the variable length bridge of the 1,4-diazacycloalkane compound desired.

I claim:

1. A method for preparing a polysubstituted 2-keto-1,4-diazacycloalkane compound comprising reacting a diamine selected from the group consisting of an acyclic 1,2-diamine and an acyclic 1,3-diamine, with a cyanohydrin acetate selected from the group consisting of an acyclic cyanohydrin acetate and a cyclic cyanohydrin acette, in the presence of (i) alkali metal hydroxide, and (ii) a haloform; forming a piperazinone when said 1,2-diamine is reacted, and a 1,4-diazepin-2-one when said 1,3-diamine is reacted; and, recovering said compound.

2. The method of claim 1 wherein said alkali metal hydroxide is added as an aqueous solution in an amount from about one equivalent to about three equivalents per mol of said diamine.

3. The method of claim 1 wherein said acyclic 1,2-diamine and said acyclic 1,3-diamine are substituted diamines having substituents selected from aryl, cycloalkyl having from 4 to about 7 ring members, and alkyl having from 1 to about 30 carbon atoms.

4. The method of claim 1 including adding an organic solvent for said diamines and said cyanohydrin acetate.

5. The method of claim 4 including adding a phase transfer catalyst selected from the group consisting of an onium salt, a triamine and a polyether in an amount sufficient to accelerate formation of said polysubstituted 2-keto-1,4-diazacycloalkane compound.

6. The method of claim 4 wherein said cyclic cyanohydrin acetate is a cycloalkanone cyanohydrin acetate and said acyclic cyanohydrin acetate is an alkyl cyanohydrin acetate having a carbonyl moiety; and, said haloform is selected from chloroform and bromoform.

7. The method of claim 6 wherein said polysubstituted compound is formed at substantially ambient pressure and temperature below about 20° C.

8. The method of claim 7 wherein said polysubstituted compound is provided on each carbon atom adjacent the N[4] atom, with (a) two acyclic substituents, or, (b) two acyclic substituents and one cyclic substituent, or, (c) one cyclic substituent.

9. The method of claim 8 wherein said phase transfer catalyst is polyether.

* * * * *